United States Patent
Ji et al.

(10) Patent No.: US 10,662,487 B2
(45) Date of Patent: May 26, 2020

(54) PSEUDOMONAS SP. AND A PREPARATION METHOD AND APPLICATION OF BIFUNCTIONAL ENZYME PREPARATION OF PSEUDOMONAS SP

(71) Applicant: Ecology Institute, Shandong Academy of Sciences, Jinan (CN)

(72) Inventors: Lei Ji, Jinan (CN); Qiang Zhang, Jinan (CN); Guanhong Chen, Jinan (CN); Jianing Wang, Jinan (CN); Xiaowen Fu, Jinan (CN); Fanyong Song, Jinan (CN); Tianyuan Li, Jinan (CN)

(73) Assignee: Ecology Institute, Shandong Academy of Sciences, Jinan (CN)

( * ) Notice: Subject to any disclaimer, the term of this patent is extended or adjusted under 35 U.S.C. 154(b) by 0 days.

(21) Appl. No.: 16/312,309

(22) PCT Filed: Jun. 12, 2018

(86) PCT No.: PCT/CN2018/090834
§ 371 (c)(1),
(2) Date: Dec. 21, 2018

(87) PCT Pub. No.: WO2019/001269
PCT Pub. Date: Jan. 3, 2019

(65) Prior Publication Data
US 2019/0376153 A1    Dec. 12, 2019

(30) Foreign Application Priority Data
Jun. 28, 2017 (CN) .......................... 2017 1 0508652

(51) Int. Cl.
*C12N 1/20* (2006.01)
*A62D 3/02* (2007.01)
*C12R 1/40* (2006.01)

(52) U.S. Cl.
CPC .................. *C12R 1/40* (2013.01); *A62D 3/02* (2013.01); *C12N 1/20* (2013.01); *C12N 2500/74* (2013.01)

(58) Field of Classification Search
None
See application file for complete search history.

*Primary Examiner* — Robert J Yamasaki
*Assistant Examiner* — Charles Zotlan Constantine
(74) *Attorney, Agent, or Firm* — CBM Patent Consulting, LLC

(57) ABSTRACT

A *Pseudomonas* sp. ECO-1 strain was preserved at the China General Microbiological Culture Collection Center (CGMCC) on Mar. 31, 2017, with the preservation number of CGMCC No. 13960. The *Pseudomonas* sp. ECO-1 strain was separated from POPs (Persistent Organic Pollutants) polluted soil for the first time. The bifunctional enzyme preparation capable of efficiently degrading polychlorinated biphenyl and atrazine was prepared by utilizing the strain for the first time; especially, the bifunctional enzyme preparation has remarkable degradation activity on the polychlorinated biphenyl which is difficult to degrade under an aerobic condition, which is completely different from functions of existing known *Pseudomonas* sp. and enzyme preparations thereof.

7 Claims, No Drawings
Specification includes a Sequence Listing.

PSEUDOMONAS SP. AND A PREPARATION METHOD AND APPLICATION OF BIFUNCTIONAL ENZYME PREPARATION OF PSEUDOMONAS SP

BACKGROUND OF THE INVENTION

Technical Field

The present invention relates to a *Pseudomonas* sp. and a preparation method and application of a bifunctional enzyme preparation of the *Pseudomonas* sp., belonging to the technical field of environmental biology.

Description of Related Art

Persistent organic pollutants (POPs) are a type of organic pollutant in the environment that are persistent, semi-volatile, bioaccumulative and highly toxic and have long-distance migration. They are widely distributed and harmful to humans. Among them, the industrial chemicals polychlorinated biphenyls (PCBs) were the first POPs included in the international Stockholm Convention. The higher the degree of chlorination, the greater the toxicity and the more difficult the PCBs are to decompose. The organochlorine pesticide atrazine is a long half-life triazine herbicide and seriously pollutes soil, aquatic ecosystems and drinking water sources because of its high mobility. The organochlorine pesticide atrazine thus has been nominated by the academic community as a new POP substance. At present, the existing problem of POPs-caused pollution has to be solved urgently. New POPs-caused pollution accidents continue to occur, and timely and effective treatment and restoration of polluted environments are essential for human health and economic development.

Microbial degradation is recognized as an environmentally friendly and effective means of controlling POPs-caused pollution because it has the excellent advantages of low consumption and ease in achieving in-situ remediation, is environmental safe and a pure ecological processes. Aerobic microorganisms can oxidize low-chlorinated PCBs (nCl<5) to chlorobenzoates, but hardly degrade high-chlorinated PCBs (nCl≥5); anaerobic biological processes reduce high-chlorinated PCBs to low-chlorinated PCBs, but cannot destroy the benzene ring structures. At present, microbial degradation of PCBs has a long cycle and low efficiency, and efficient degradation of high-chlorinated PCBs under aerobic conditions has not been reported. Hujiang et al. used *Arthrobacter* sp. Hal to achieve efficient degradation of atrazine in 84 h. However, multi-functional enzymes capable of simultaneously efficiently degrading different types of POPs are still blank at home and abroad. In view of the fact that soil and aquatic ecosystem pollution is not caused by a single pollution factor, the preparation of multifunctional enzymes capable of efficiently degrading POPs and improving the degradation rate of PCBs and organochlorine pesticides is of great significance for promoting large-scale rapid restoration of polluted environments.

BRIEF SUMMARY OF THE INVENTION

The present invention is intended to supplement the deficiencies of the prior art, and provides a *Pseudomonas* sp. derived from POPs-polluted soil and capable of degrading polychlorinated biphenyls and atrazine and a preparation method and application of a bifunctional enzyme preparation of the *Pseudomonas* sp.

The present invention is implemented by the following technical solution:

A *Pseudomonas* sp. ECO-1 strain was preserved at the China General Microbiological Culture Collection Center (CGMCC) (Address: Institute of Microbiology, Chinese Academy of Sciences, No. 3, Yard No. 1, Beichen West Road, Chaoyang District, Beijing) on Mar. 31, 2017, with the preservation number of CGMCC No. 13960.

The *Pseudomonas* sp. ECO-1 strain is screened by the following method:

A POPs-polluted soil leaching solution is prepared and diluted to 5 concentration gradients: $10^{-1}$, $10^{-2}$, $10^{-3}$, $10^{-4}$, and $10^{-5}$, respectively. The diluted bacterial suspension is applied to a solid medium containing polychlorinated biphenyls and atrazine, and the operation is carried out twice in parallel for each concentration and then the diluted bacterial suspension is cultured at 30° C. for 1-3 days. Bacterial colonies with faster growth and typical morphology are picked out, and then are subjected to plate scribing three times for separation and purification, and single colonies are cultured in an inorganic salt liquid medium under the conditions of a temperature of 30° C. and a rotation speed of 150 rpm for 3 days; 1.5 mL of the culture is taken out and added with 0.5 mL of glycerol; the mixture is mixed to be uniform and then stored in a refrigerator at −80° C. for a long time. The solid medium to which the bacterial suspension is applied is an LB solid medium which comprises the following components: 10 g of peptone, 5 g of yeast extract, 10 g of sodium chloride and 20 g of agar, and the balance of water, with a natural pH. The inorganic salt liquid medium used for culturing the single colonies comprises the following components: 0.5 g of monopotassium phosphate, 0.5 g of disodium hydrogen phosphate, 0.2 g of magnesium sulfate, 0.1 g of calcium chloride, 0.2 g of sodium chloride, 1.0 g of ammonium sulfate and 2.0 g of peptone, and the balance of water, with a pH of 7.0.

The obtained strain is inoculated on the inorganic salt liquid medium containing polychlorinated biphenyls and atrazine, and cultured under the conditions of a temperature of 30° C. and a rotation speed of 150 rpm for 72 h; the turbidity of the bacterial solution is observed, and the bacterial suspension is taken to have absorbance detection at 600 nm. An enzyme-producing strain is selected according to the above indicators. The strain having the highest absorbance value in the inorganic salt medium is picked up and cultured on an LB solid medium, and preserved and recorded as ECO-1.

The *Pseudomonas* sp. ECO-1 strain is determined to have a gene sequence length of 16S rRNA being 1401 bp and a nucleotide sequence as shown in SEQ ID NO.1. By using the BLASTN program of the National Center for Biotechnology Information (NCBI), the gene sequence of the 16S rRNA of the strain of the present invention and the gene sequence of the 16S rRNA of NCBI-registered *Pseudomonas* stand strains have higher homology. After comparison, the strain of the present invention has the closest relationship with the standard strains *Pseudomonas putida* ATCC 12633 and *Pseudomonas asplenii* ATCC23835, with the similarity of 99%, but there is no report that *Pseudomonas* sp. can degrade various POPs.

The basic method for sequencing the above-mentioned 16S rRNA gene is to: prepare the genomic DNA of a strain by using a bacterial genome extraction kit (Tiangen); with the genomic DNA of the strain as a template, use a universal primer of the bacterial 16S rRNA gene for amplification, purify the PCR amplification product by using a gel extraction kit (Tiangen); after electrophoresis verification, sequence the 16S rRNA gene by Qingdao Tsingke Yuxi Biotechnology Co., Ltd., and compare the obtained sequence with the gene sequence of 16S rRNA of the standard strain included in the National Center for Bioinformatics (NCBI).

A method for producing a bifunctional enzyme preparation by using the *Pseudomonas* sp. ECO-1 strain, comprising the following steps:

(1) scribing the *Pseudomonas* sp. ECO-1 strain on an LB solid medium, and carrying out inverted activation culture at 28-37° C. for 1-2 days to prepare an activated strain;

(2) inoculating the activated strain prepared in Step (1) into the LB liquid medium, and carrying out a shake culture for 1-2 days under the conditions of a temperature of 28-37° C. and a rotation speed of 100-200 rpm to prepare a seed solution;

(3) inoculating the seed solution prepared in Step (2) into an inorganic salt medium at a volume percentage of 1-10%, and carrying out enlargement culture under the conditions of a temperature of 28-37° C. and a rotation speed of 100-200 rpm for 3-5 days to prepare a *Pseudomonas* sp. ECO-1 solution; and (4) centrifuging the *Pseudomonas* sp. ECO-1 solution prepared in Step (3) at a rotation speed of 3,000-10,000 rpm for 2-10 minutes, collecting thalli, and suspending them in a 10-30-fold by volume phosphate buffer solution with the pH of 6.0-8.0, carrying out ultrasonic cell disruption, centrifuging them under the conditions of a temperature of 4-25° C. and a rotation speed of 3,000-8,000 rpm for 2-5 minutes, and collecting the supernatant to obtain a bifunctional enzyme preparation.

Preferably according to the present invention, the LB solid medium in Step (1) comprises the following components per liter:

10 g of peptone, 5 g of a yeast extract, 10 g of sodium chloride and 20 g of agar, and the balance of water, with a natural pH.

Preferably according to the present invention, the LB liquid medium in Step (2) comprises the following components per liter:

10 g of peptone, 5 g of a yeast extract and 10 g of sodium chloride, and the balance of water, with a natural pH.

Preferably according to the present invention, the inorganic salt medium in Step (3) comprises the following components per liter:

0.5 g of monopotassium phosphate, 0.5 g of disodium hydrogen phosphate, 0.2 g of magnesium sulfate, 0.1 g of calcium chloride, 0.2 g of sodium chloride, 1.0 g of ammonium sulfate, 2.0 g of peptone, 0.5 g of biphenyl, 0.025 g of atrazine and the balance of water, with a pH of 7.0.

Preferably according to the present invention, the ultrasonic cell disruption in Step (4) is carried out under the following conditions:

the disruption time/gap time is 2 s/2 s, the total time is 17 min, and the power is 165 W.

Application of the bifunctional enzyme preparation for degrading polychlorinated biphenyls and atrazine.

The application comprises the following steps:

taking the prepared bifunctional enzyme preparation, adjusting the concentrations of polychlorinated biphenyls and/or atrazine in the system to 0.5-5 mg/L and 50-500 mg/L, respectively, adding the bifunctional enzyme preparation until the bifunctional enzyme preparation concentration in the system reaches 0.05-0.25 g/L, and reacting for 3-24 h at a temperature of 20-37° C.

Beneficial Effect

The *Pseudomonas* sp. ECO-1 strain is separated from POPs (Persistent Organic Pollutants) polluted soil for the first time; the bifunctional enzyme preparation capable of efficiently degrading polychlorinated biphenyl and atrazine is prepared by utilizing the strain for the first time; especially, the bifunctional enzyme preparation has remarkable degradation activity on the polychlorinated biphenyl which is difficult to degrade under an aerobic condition, which is completely different from the functions of existing known *Pseudomonas* sp. and the enzyme preparations thereof. The bifunctional enzyme preparation has a large-scale production and application prospect.

DETAILED DESCRIPTION OF THE INVENTION

The technical solution of the present invention will be further described below with reference to the embodiments, but the scope of protection of the present invention is not limited thereto.

Embodiment 1

A *Pseudomonas* sp. ECO-1 strain was preserved at the China General Microbiological Culture Collection Center (CGMCC) (Address: Institute of Microbiology, Chinese Academy of Sciences, No. 3, Yard No. 1, Beichen West Road, Chaoyang District, Beijingon) on Mar. 31, 2017, with the preservation number of CGMCC No. 13960.

The *Pseudomonas* sp. ECO-1 strain is screened by the following method:

A POPs-polluted soil leaching solution is prepared and diluted to 5 concentration gradients: $10^{-1}$, $10^{-2}$, $10^{-3}$, $10^{-4}$, and $10^{-5}$, respectively. The diluted bacterial suspension is applied to a solid medium containing polychlorinated biphenyls and atrazine, and the operation is carried out twice in parallel for each concentration; and then the diluted bacterial suspension is cultured at 30° C. for 1-3 days. Bacterial colonies with faster growth and typical morphology are picked out, and then are subjected to plate scribing three times for separation and purification, and single colonies are cultured in an inorganic salt liquid medium under the conditions of a temperature of 30° C. and a rotation speed of 150 rpm for 3 days; 1.5 mL of the culture is taken out and added with 0.5 mL of glycerol; the mixture is mixed to be uniform and then stored in a refrigerator with a temperature of −80° C. for a long time. The solid medium to which the bacterial suspension is applied is an LB solid medium which comprises the following components: 10 g of peptone, 5 g of yeast extract, 10 g of sodium chloride, 20 g of agar, and the balance of water, with a natural pH. The inorganic salt liquid medium used for culturing the single colonies comprises the following components: 0.5 g of monopotassium phosphate, 0.5 g of disodium hydrogen phosphate, 0.2 g of magnesium sulfate, 0.1 g of calcium chloride, 0.2 g of sodium chloride, 1.0 g of ammonium sulfate, 2.0 g of peptone, and the balance of water, with a pH of 7.0.

The obtained strain is inoculated on the inorganic salt liquid medium containing polychlorinated biphenyls and atrazine, and cultured under the conditions of a temperature of 30° C. and a rotation speed of 150 rpm for 72 h; the turbidity of the bacterial solution is observed, and the bacterial suspension is taken to have absorbance detection at 600 nm. An enzyme-producing strain is selected according to the above indicators. The strain having the highest absorbance value in the inorganic salt medium is picked up and cultured on an LB solid medium, and preserved and recorded as ECO-1.

The *Pseudomonas* sp. ECO-1 strain is determined to have a gene sequence length of 16S rRNA being 1401 bp and a nucleotide sequence as shown in SEQ ID NO.1. By using the BLASTN program of the National Center for Biotechnology Information (NCBI), the gene sequence of the 16S rRNA of the strain of the present invention and the gene sequence of the 16S rRNA of NCBI-registered *Pseudomonas* stand strains have higher homology. After comparison, the strain of the present invention has the closest relationship with the standard strains *Pseudomonas putida* ATCC 12633 and *Pseudomonas asplenii* ATCC23835, with the similarity of 99%, but there is no report that *Pseudomonas* sp. can degrade various POPs.

The basic method for sequencing the above-mentioned 16S rRNA gene is to: prepare the genomic DNA of a strain by using a bacterial genome extraction kit (Tiangen); with the genomic DNA of the strain as a template, use a universal primer of the bacterial 16S rRNA gene for amplification, purify the PCR amplification product by using a gel extraction kit (Tiangen); after electrophoresis verification, sequence the 16S rRNA gene by Qingdao Tsingke Yuxi Biotechnology Co., Ltd., and compare the obtained sequence with the gene sequence of 16S rRNA of the standard strain included in the National Center for Bioinformatics (NCBI).

Embodiment 2

A method for producing a bifunctional enzyme preparation using the *Pseudomonas* sp. ECO-1 strain, comprising the following steps:
(1) scribing the *Pseudomonas* sp. ECO-1 strain on an LB solid medium from a refrigerator with a temperature of −80° C., and carrying out inverted activation culture at 28 for 1 day,
wherein the LB solid medium comprises the following components per liter:
10 g of peptone, 5 g of a yeast extract, 10 g of sodium chloride, 20 g of agar, and the balance of water, with a natural pH;
(2) picking ECO-1 single colonies into the LB liquid medium, and carrying out a shake culture for 1 day under the conditions of a temperature of 28° C. and a rotation speed of 200 rpm to prepare a seed solution,
wherein the LB liquid medium comprises the following components per liter:
10 g of peptone, 5 g of yeast extract, 10 g of sodium chloride, and the balance of water, with a natural pH;
(3) inoculating the seed solution prepared in Step (2) into an inorganic salt medium at a volume percentage of 10%, and carrying out enlargement culture under the conditions of a temperature of 28° C. and a rotation speed of 200 rpm for 5 days to prepare a *Pseudomonas* sp. ECO-1 solution,
wherein the inorganic salt medium comprises the following components per liter:
0.5 g of monopotassium phosphate, 0.5 g of disodium hydrogen phosphate, 0.2 g of magnesium sulfate, 0.1 g of calcium chloride, 0.2 g of sodium chloride, 1.0 g of ammonium sulfate, 2.0 g of peptone, 0.5 g of biphenyl, 0.025 g of atrazine and the balance of water, with a pH of 7.0; and
(4) centrifuging the *Pseudomonas* sp. ECO-1 solution prepared in Step (3) at a rotation speed of 3,000 rpm for 10 minutes, collecting thalli, and suspending in a 30-fold by volume phosphate buffer solution with a pH of 7.0, carrying out ultrasonic cell disruption, centrifuging under the conditions of a temperature of 4° C. and a rotation speed of 3,000 rpm for 2 minutes, and collecting the supernatant to obtain a bifunctional enzyme preparation,
wherein the ultrasonic cell disruption is carried out under the following conditions:
the disruption time/gap time is 2 s/2 s, the total time is 17 min, and the power is 165 W.

Reference Examples

Same as the method described in Embodiment 2, except that the strain used is *Pseudomonas putida* ATCC 12633.

Experimental Example 1 Analysis of the Biodegradability of the Bifunctional Enzyme to Polychlorinated Biphenyls A pentachlorobiphenyl PCB114 substrate with a concentration of 25 mg/L, a bifunctional enzyme and a PBS buffer are mixed at a ratio of 1:5:19 (volume ratio), and then react under the conditions of a temperature of 30° C. and pH of 7.0 for 12 h; 10 mL of n-hexane is added to carry out extraction 3 times; the extract is taken to detect the degradation rate of pentachlorobiphenyl by a GC-MS method, and the degradation rate of the PCB114 reaches 65.7%.

In a reference example, the intracellular enzyme of a strain *Pseudomonas putida* ATCC 12633, a PBS buffer solution and a pentachlorobiphenyl PCB114 substrate with a concentration of 25 mg/L are mixed at a ratio of 5:19:1 (volume ratio) and then react under the conditions of a temperature of 30° C. and pH of 7.0 for 12 h; 10 mL of n-hexane is added to carry out extraction 3 times; the extract is taken to detect the degradation rate of pentachlorobiphenyl by a GC-MS method, and the PCB114 is not degraded.

Experimental Example Analysis of the Biodegradability of the Bifunctional Enzyme to Atrazine An atrazine substrate with a concentration of 100 mg/L, a bifunctional enzyme and a PBS buffer solution are mixed at a ratio of 1:10:38 (volume ratio), and then react under the conditions of a temperature of 25° C. and pH of 7.5 for 6 h; 10 mL of dichloromethane is added to carry out extraction 3 times; the extract is taken to detect the degradation rate of atrazine by an HPLC method, and the degradation rate reaches 45%.

In a reference example, the intracellular enzyme of a strain *Pseudomonas putida* ATCC 12633, a PBS buffer solution, and an atrazine substrate with a concentration of 100 mg/L are mixed at a ratio of 10:38:1 (volume ratio) and then react under the conditions of a temperature of 25° C. and pH of 7.5 for 6 h; 10 mL of dichloromethane is added to carry out extraction 3 times; the extract is taken to detect the degradation rate of atrazine by the HPLC method, and the degradation rate is 7.3%.

The results show that the bifunctional enzyme prepared from the *Pseudomonas* sp. ECO-1 strain can degrade polychlorinated biphenyls and atrazine efficiently, and especially has higher degradation activity for high-chlorinated polychlorinated biphenyls which are difficult to degrade under aerobic conditions. The the bifunctional enzyme therefore has a potential application value in the field of POPs-caused pollution control and restoration. In the reference examples, the intracellular enzyme of *Pseudomonas putida* ATCC 12633, a *Pseudomonas putida* standard strain with high homology with the *Pseudomonas* sp. ECO-1, has no degradability to high-chlorinated polychlorinated biphenyls under aerobic conditions and its degradation rate to atrazine is much lower than that of the intracellular enzyme of the *Pseudomonas* ECO-1 strain. The bifunctional enzyme prepared from the *Pseudomonas* sp. ECO-1 strain is a multifunctional enzyme capable of simultaneously efficiently degrading different types of POPs, which is completely different from the functions of the existing known *Pseudomonas* sp. and enzyme preparations thereof. The bifunctional enzyme preparation has a large-scale production and application prospect.

What is claimed is:

1. A method for producing a bifunctional enzyme preparation by using a *Pseudomonas* sp. ECO-1 strain deposited at the China General Microbiological Culture Collection Center (CGMCC) under CGMCC accession number CGMCC No. 13960, comprising the following steps:

(1) streaking the *Pseudomonas* sp. ECO-1 strain on an LB solid medium, and carrying out inverted activation culture at 28-37° C. for 1-2 days to prepare an activated strain;

(2) inoculating the activated strain prepared in Step (1) into a LB liquid medium, and carrying out a shake culture for 1-2 days under the conditions of a temperature of 28-37° C. and a rotation speed of 100-200 rpm to prepare a seed solution;

(3) inoculating the seed solution prepared in Step (2) into an inorganic salt medium at a volume percentage of 1-10%, and carrying out enlargement culture under the conditions of a temperature of 28-37° C. and a rotation speed of 100-200 rpm for 3-5 days to prepare a *Pseudomonas* sp. ECO-1 solution;

(4) centrifuging the *Pseudomonas* sp. ECO-1 solution prepared in Step (3) at a rotation speed of 3,000-10,000 rpm for 2-10 minutes to obtain a cell pellet, collecting the cell pellet, and resuspending the collected cell pellet in a 10-30-fold by volume phosphate buffer solution with the pH of 6.0-8.0; and, (5) carrying out ultrasonic cell disruption on the resuspended cells to produce disrupted cell suspension, centrifuging the disrupted cell suspension under the conditions of a temperature of 4-25° C. and a rotation speed of 3,000-8,000 rpm for 2-5 minutes to produce a supernatant, and collecting the supernatant to obtain a bifunctional enzyme preparation.

2. The method of claim 1, wherein the LB solid medium in Step (1) comprises the following components per liter: 10 g of peptone, 5 g of a yeast extract, 10 g of sodium chloride, 20 g of agar, and the balance of water, with a pH of 7.0.

3. The method of claim 1, wherein the LB liquid medium in Step (2) comprises the following components per liter: 10 g of peptone, 5 g of yeast extract, 10 g of sodium chloride, and the balance of water, with a pH of 7.0.

4. The method of claim 1, wherein the inorganic salt medium in Step (3) comprises the following components per liter:

0.5 g of monopotassium phosphate, 0.5 g of disodium hydrogen phosphate, 0.2 g of magnesium sulfate, 0.1 g of calcium chloride, 0.2 g of sodium chloride, 1.0 g of ammonium sulfate, 2.0 g of peptone, 0.5 g of biphenyl, 0.025 g of atrazine and the balance of water, with a pH of 7.0.

5. The method of claim 1, wherein the ultrasonic cell disruption in Step (5) is carried outer under the following conditions: the disruption time/gap time is 2 s/2 s, the total time is 17 min, and the power is 165 W.

6. A process for treating polluted soils comprising administering the bifunctional enzyme preparation produced by the method of claim 1 to a soil polluted with polychlorinated biphenyls and/or atrazine.

7. The process of claim 6, wherein the step of administrating comprises the following steps:

adjusting the amount of polluted soil to achieve a concentration of polychlorinated biphenyls and/or atrazine at 0.5-5 mg/L and 50-500 mg/L, respectively;

adding the bifunctional enzyme preparation to 0.05-0.25 g/L; and performing the reaction for 3-24 h at a temperature of 20-37° C.

* * * * *

SEQUENCE LISTING

```
<160> NUMBER OF SEQ ID NOS: 1

<210> SEQ ID NO 1
<211> LENGTH: 1401
<212> TYPE: DNA
<213> ORGANISM: Pseudomonas sp. 101

<400> SEQUENCE: 1
gtcctcccga ggttagacta gctacttctg gtgcacccac tcccatggtg tgacgggcgg      60
tgtgtacaag gcccgggaac gtattcaccg cgacattctg attcgcgatt actagcgatt     120
ccgacttcac gcagtcgagt tgcagactgc gatccggact acgatcggtt ttgtgagatt     180
agctccacct cgcggcttgg caaccctctg taccgaccat tgtagcacgt gtgtagccca     240
ggccgtaagg gccatgatga cttgacgtca tccccacctt cctccggttt gtcaccggca     300
gtctccttag agtgcccacc ataacgtgct ggtaactaag gacaagggtt gcgctcgtta     360
cgggacttaa cccaacatct cacgacacga gctgacgaca gccatgcagc acctgtgtca     420
gagttcccga aggcaccaat ccatctctgg aaagttctct gcatgtcaag gcctggtaag     480
gttcttcgcg ttgcttcgaa ttaaaccaca tgctccaccg cttgtgcggg cccccgtcaa     540
ttcatttgag ttttaacctt gcggccgtac tccccaggcg gtcaacttaa tgcgttagct     600
gcgccactaa aatctcaagg attccaacgg ctagttgaca tcgtttacgg cgtggactac     660
cagggtatct aatcctgttt gctccccacg ctttcgcacc tcagtgtcag tatcagtcca     720
ggtggtcgcc ttcgccactg gtgttccttc ctatatctac gcatttcacc gctacacagg     780
aaattccacc accctctacc gtactctagc ttgccagttt tggatgcagt tcccaggttg     840
agcccggggc tttcacatcc aacttaacaa accacctacg cgcgctttac gcccagtaat     900
tccgattaac gcttgcaccc tctgtattac cgcggctgct ggcacagagt tagccggtgc     960
ttattctgtc ggtaacgtca aaacactaac gtattaggtt aatgcccttc ctcccaactt    1020
aaagtgcttt acaatccgaa gaccttcttc acacacgcgg catggctgga tcaggctttc    1080
gcccattgtc caatattccc cactgctgcc tcccgtagga gtctggaccg tgtctcagtt    1140
ccagtgtgac tgatcatcct ctcagaccag ttacggatcg tcgccttggt gagccattac    1200
ctcaccaact agctaatccg acctaggctc atctgatagc gcaaggcccg aaggtcccct    1260
gctttctccc gtaggacgta tgcggtatta gcgttccttt cgaaacgttg tccccacta    1320 ccaggcagat tcctaggcat tactcacccg tccgccgctg aatcgaagag caagctttct    1380
catccgctcg actgcaggta g                                              1401
```